United States Patent
Korpan et al.

(10) Patent No.: US 6,468,269 B1
(45) Date of Patent: Oct. 22, 2002

(54) CRYOGENIC SYSTEM, ESPECIALLY FOR PERFORMING CRYOSURGICAL SURGERY

(76) Inventors: Nikolai Korpan, Kaasgrabengasse 52/3/5, A-1190 Vienna (AT); Jaroslav Zharkov, A/c 376/7, Kiew 252146 (UA)

( * ) Notice: Subject to any disclaimer, the term of this patent is extended or adjusted under 35 U.S.C. 154(b) by 0 days.

(21) Appl. No.: 09/674,357

(22) PCT Filed: Feb. 29, 2000

(86) PCT No.: PCT/AT00/00053
§ 371 (c)(1),
(2), (4) Date: Oct. 31, 2000

(87) PCT Pub. No.: WO00/51509
PCT Pub. Date: Sep. 8, 2000

(30) Foreign Application Priority Data

Mar. 2, 1999 (AT) .................................................. 347/99
Apr. 26, 1999 (AT) .................................................. 729/99
Feb. 23, 2000 (AT) .................................................. 279/00

(51) Int. Cl.$^7$ .............................................. A61B 18/18
(52) U.S. Cl. ........................................... 606/23; 606/24
(58) Field of Search ..................................... 606/20–26

(56) References Cited

U.S. PATENT DOCUMENTS

| | | | |
|---|---|---|---|
| 4,269,390 A | 5/1981 | Bryne | |
| 4,345,598 A | 8/1982 | Zobac et al. | |
| 4,412,538 A | * 11/1983 | Yamauchi et al. | 606/24 |
| 5,667,505 A | * 9/1997 | Straus | 606/24 |
| 5,674,218 A | 10/1997 | Rubinsky et al. | |
| 5,709,203 A | 1/1998 | Gier | |
| 6,251,105 B1 | * 6/2001 | Mikus et al. | 606/22 |

FOREIGN PATENT DOCUMENTS

| | | |
|---|---|---|
| GB | 20263247 | 2/1980 |
| GB | 2289412 | 11/1995 |
| SU | 1102096 | 2/1988 |
| WO | 9304647 | 3/1993 |
| WO | 9852479 | 11/1998 |

* cited by examiner

Primary Examiner—Michael Peffley
Assistant Examiner—David M. Ruddy
(74) Attorney, Agent, or Firm—Dykema Gossett PLLC

(57) ABSTRACT

The invention relates to a cryogenic system which is provided for performing cryosurgical interventions in the area of human and veterinary medicine, especially for treating tumors. The inventive system is comprised of a cryostat (1) and of a connecting device (8) which is located between coaxial cryogenic lines for the direct flow (9) and return flow (10) of the cryogenic medium and which is provided for connecting a cryoinstrument (17) to a cryo-attachment (13). The electromagnetic valve (11) is located in the immediate proximity of the connecting device (8). A regulating device (18) is provided for controlling the electromagnetic valves (2, 3, 4 and 7) as well as the heating element (12), and regulates the excess pressure of the cryogenic medium in the cryostat (1) to an accuracy of $\pm 0.1 \times 10^5$ Pa. The bottle neck (23) of the cryostat (1) is made of a material exhibiting a low level of thermal conductivity. In order to effect a precise sealing between said coaxial lines (9) and (10), truncated connecting elements (30, 31) which correspond with one another are placed inside line (10), and truncated connecting elements (34, 35) which also correspond with one another are placed inside line (9). In addition, an electric line (36) is provided for an electrical connection or interruption between both lines (9, 10).

14 Claims, 3 Drawing Sheets ation are for example general surgery, urology, gynecology,
CRYOGENIC SYSTEM, ESPECIALLY FOR PERFORMING CRYOSURGICAL SURGERY

BACKGROUND OF THE INVENTION

1. Field of the Invention

The invention relates to a cryogenic device of the type used in medical procedures.

2. The Prior Art

The use of cryogenic systems is most extensive in cryosurgical instruments for the treatment of cancer where they are successfully employed. Further medical ranges of application are for example general surgery, urology, gynecology, otorhinolaryngology and ophthalmology, plastic surgery, gnathosurgery, orthopaedics, veterinary medicine but also phytopathology and so on.

In known cryostats of this type, thermal insulation is achieved by the space provided between the housing and the inner container which contains the cryogenic medium, a vacuum with a residual pressure of approximately $10^{-4}$ mm Hg to $10^{-6}$ mm Hg being produced in the space. Cryogenic pumps as, e.g., activated carbon or zeolite, keep the above-mentioned residual pressure permanently constant as they sorb the residual gases from the vacuum space by freezing to low temperatures to $-196°$ C.

Connecting arrangements between the coaxial lines for the direct flow and the return flow of the cryogenic medium for cryosurgical interventions in the area of medicine, e.g., to connect a cryoapplicator to a cryoinstrument, are used just as extensively in the cryosurgical instruments used for the treatment of cancer. The sealing of a cryogenic medium by means of an intermediate layer, e.g., made of copper, is achieved by known connections of this type.

Known instruments of this type have the disadvantage that the stabilization of determined working conditions with excess pressure in a cryogenic system for cryogenic action upon the biological tissue as well as the proportioning of the cryogenic medium flowing toward the various-sized working surface of the cryoinstrument can be achieved neither with accuracy nor in a continuous and permanent way, so that it is not possible to maintain the temperature determined for cryogenic action in a continuous, permanent and accurate way, so that the accurate guaranteed cryodestruction of the diseased tissue, specifically of cancerous tissue, is not secured, thus leading to a recurrence (regrowth) of the tumor.

Another drawback is that, after some time, the cryogenic pumps with activated carbon or zeolite are filled up with residual gases, thus losing their adsorbing properties. In order to restore the adsorbing properties, the cryogenic pumps (activated carbon, zeolite) must be taken out, reactivated in vacuum by heating them up to high temperatures, and inserted again. A further disadvantage is that the heat flows from the bottle neck toward the inner container affect negatively the residual pressure in the vacuum space.

With the prior art devices it is equally disadvantageous that an intermediate layer for sealing the cryogenic medium can merely be used a few times, but not very often.

It is therefore the object of the invention to improve the prior art cryogenic systems in such a manner that under determined working conditions of a cryogenic system acting in a cryogenic way upon the biological tissue, an excess pressure is accurately achieved and maintained and that the proportioning of the cryogenic medium flowing toward the various-sized working surface of the cryoinstrument can be achieved.

It is therefore another object of the invention to improve the known cryostat in such a manner that the low pressure of residual gases (approximately $10^{-4}$ to $10^{-6}$ mm Hg) is permanently kept constant inside the vacuum space so that the cryogenic pumps must not be activated repeatedly and that the heat flows from the bottle neck toward the inner container are reduced.

It is therefore still another object of the invention to improve the known connections in such a way that a cryogenic medium is accurately sealed between the coaxial lines for the direct flow and the return flow of the cryogenic medium with an electric line for an electrical connection or interruption between both lines in the cryosurgical instruments, e.g., in case of frequent applications of various cryoapplicators and cryoinstruments.

The invention provides a cryogenic system with a regulating device for controlling the electromagnetic valves and the heating element, one electromagnetic valve being located at a distance from the connecting device and a heating element being located in the line for the return flow of the evaporated cryogenic medium, so that a determined temperature measured by the temperature detector is reached with an accuracy of $\pm 1°$ C. as a result of the opening and closing of an electromagnetic valve.

The invention provides for a cryostat used to keep permanently constant the low pressure of residual gases so that the necessary residual pressure is maintained.

An improved connecting device located between the coaxial lines for the direct flow and the return flow of the cryogenic medium has been developed and is used in cryosurgical instruments utilized for cryosurgical interventions in medicine, e.g., to connect a cryoapplicator to a cryoinstrument in the treatment of cancer.

BRIEF DESCRIPTION OF THE DRAWINGS

The invention will be described in more detail with the help of a schematic illustration of the device and the drawings, wherein.

DETAILED DESCRIPTION OF THE PREFERRED EMBODIMENT

Figure 1:
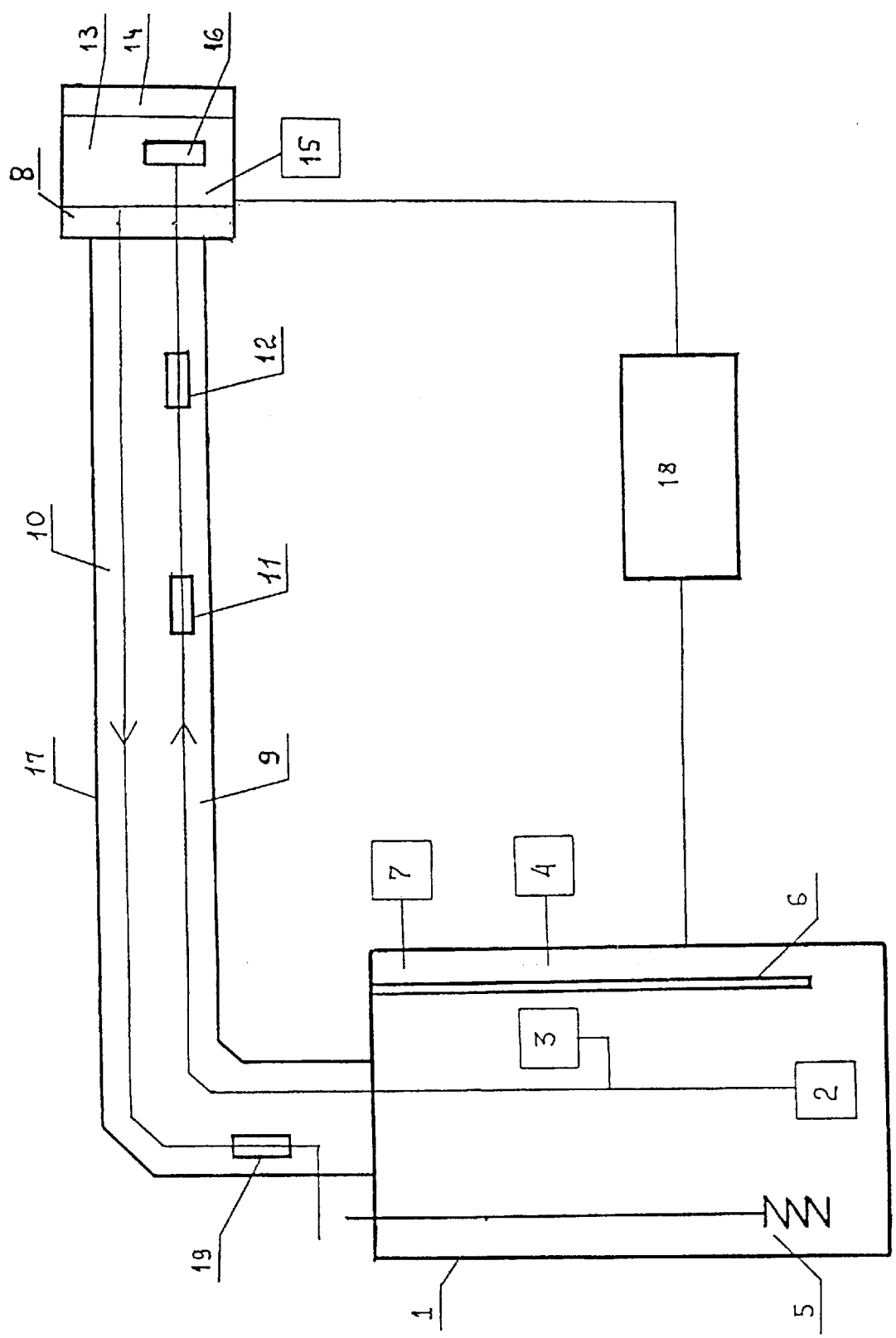
FIG. 1 shows a longitudinal section of a cryogenic system.

As shown in FIG. 1, the cryogenic system for cryosurgical interventions in the area of human and veterinary medicine, especially for treating tumors, as well as in phytopathology, includes a cryostat (1) including an electromagnetic valve (2) for a liquid cryogenic medium, an electromagnetic valve (3) for a gaseous cryogenic medium, an electromagnetic valve (4) for regulating the excess pressure of the cryogenic medium, a heating device (5) for heating the cryogenic medium, a sensor (6) for detecting the level of cryogenic medium and a pressure sensor (7), and of a connecting device (8) located between the coaxial cryogenic lines for the direct flow (9) and the return flow (10) of the cryogenic medium, the line (9) communicating with the cryostat (1) via the electromagnetic valve (2), an electromagnetic valve (11) and a heater (12) being arranged in the line (9) for connecting a cryotube (17) to a cryoapplicator (13), the cryoapplicator being provided with a working surface (14), a chamber for heat exchange (15) and a temperature detector (16).

In order to continuously stabilize a determined operating temperature of a cryogenic system for cryogenic action upon biological tissue and in order to secure the guaranteed cryodestruction of the cancerous tissue in particular, the electromagnetic valve (11) is located in immediate proximity to the connecting device (8). A controllable heating element (12) is additionally provided between the valve (11) and the connecting device (8).

A regulating device (18) is provided for controlling the electromagnetic valves (2, 3, 4 and 7) as well as the heating element (12), the regulating device regulating the excess pressure of the cryogenic medium in the cryostat (1) to an accuracy of $\pm 0.1 + 10^5$ Pa.

The electromagnetic valve (11) is located at a distance from the connecting device (8) that is less than $\frac{1}{12}$, preferably less than $\frac{1}{14}$, of the cryotube's (17) length.

In the line (10) for the return flow of the evaporated cryogenic medium there is arranged a heating element (19).

A temperature detector (16) is provided in the cryoapplicator (13) so that a determined temperature measured by the temperature detector (16) is reached by stabilizing the pressure and by continuously proportioning the cryogenic medium flowing to the working surface (14) of the cryoapplicator (13) to an accuracy of $\pm 1°$ C. as a result of the opening and closing of the electromagnetic valve (11) on the working surface (14) of the cryoapplicator (13), and that finally the cryogenic medium is heated to room temperature in the heater (19) prior to being discharged out of the chamber for heat exchange (15) through the cryogenic line (10) of the cryotube (17) into the atmosphere.

Figure 2:
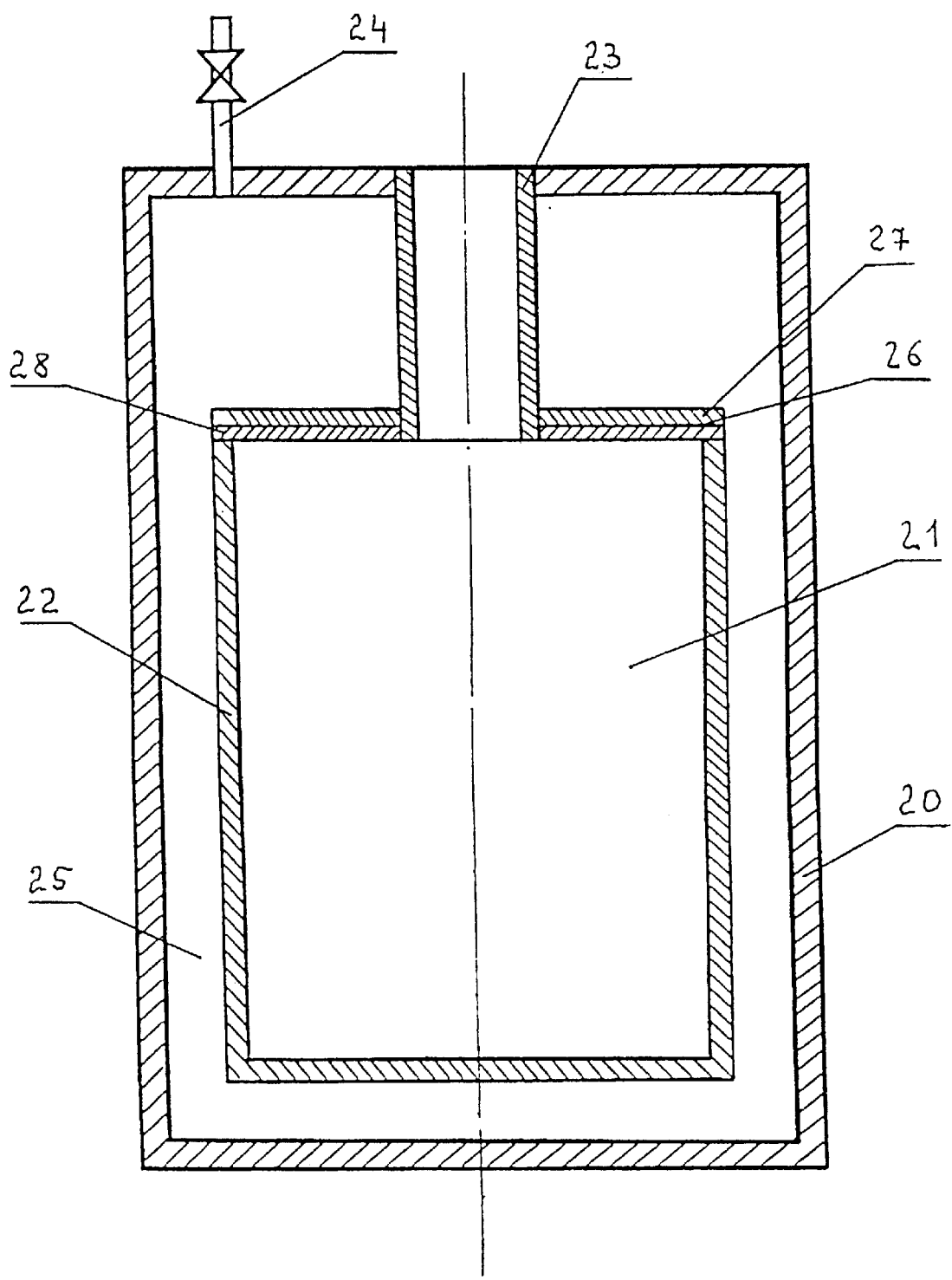
FIG. 2 shows a longitudinal section of a cryostat.

According to FIG. 2, the cryostat includes an external housing (20), an inner container (21) with a wall (22), both being joined by a bottle neck (23), furthermore of a pump-down device (24) as well as of a vacuum space (25) for thermal insulation. In order to keep permanently constant the low pressure of residual gases, the wall (22) of the inner container (21) in the vacuum space (25) is made of an aluminium alloy which gets a porous structure from the side of the vacuum space (25) by way of chemical surface treatment, e.g., by etching, so that the residual gases are sorbed at low temperatures in the vacuum space (25), thus allowing the necessary residual pressure to be maintained.

To reduce the flows of heat from the bottle neck (23) toward the inner container (21), the bottle neck (23) is formed of a low thermal conductivity material, e.g., of stainless steel, and the upper wall of the inner container (21) of a bimetallic plate (26), whose upper portion (27) is made of a stainless steel and the lower portion (28) of an aluminium alloy, both portions (27, 28) being diffusion bonded over the entire plane.

Figure 3:
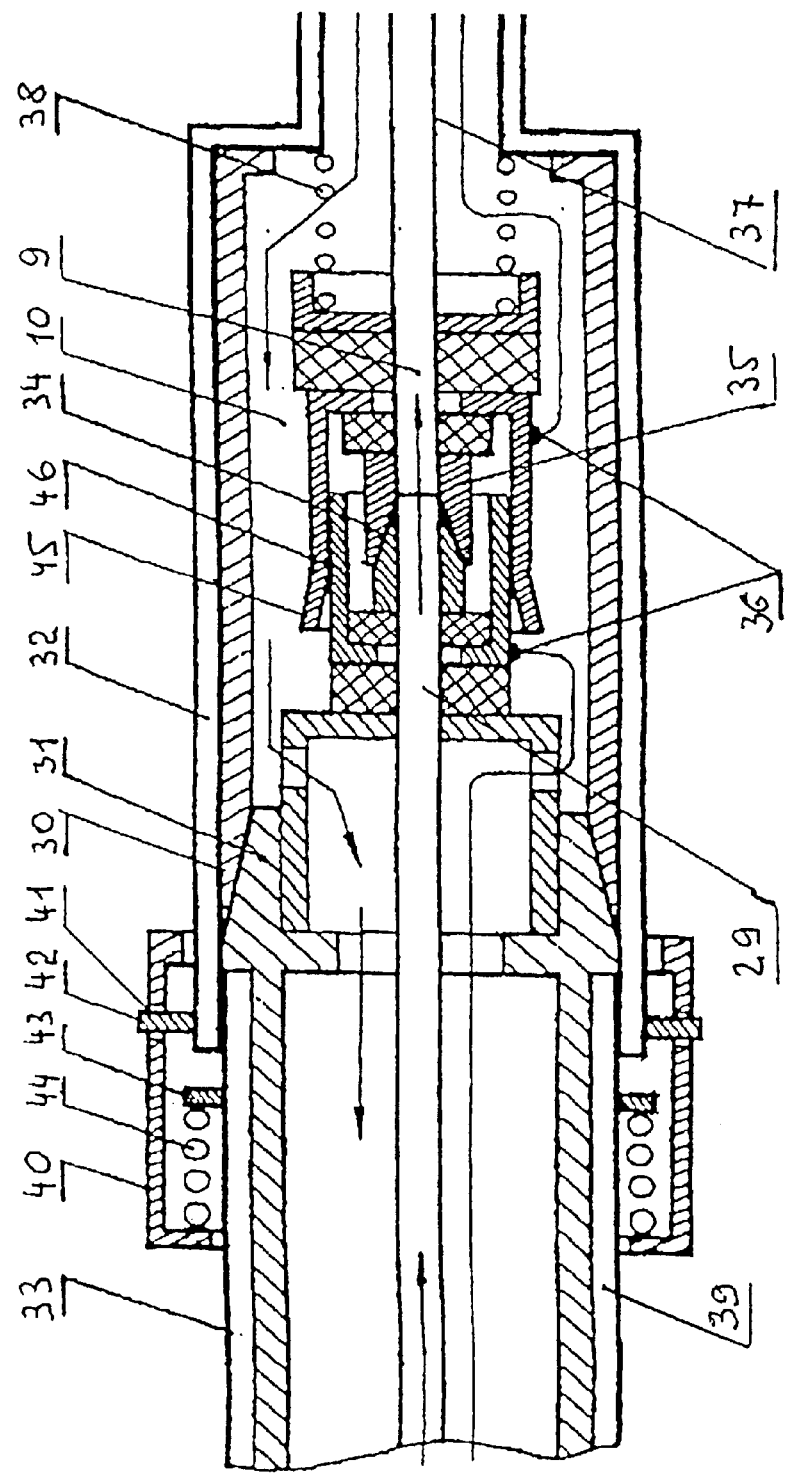
FIG. 3 shows a longitudinal section of a connecting device located between the coaxial lines for the direct flow and the return flow of the cryogenic medium.

As shown in FIG. 3, in the connection device the cryogenic system of the invention is fitted, between the coaxial lines for the direct flow (9) and for the return flow (10) of the cryogenic medium (29) in cryosurgical instruments for cryosurgical interventions in the area of medicine, e.g., for connecting a cryoapplicator with a cryoinstrument, with connecting elements (30, 31, 34, 35) for the accurate sealing between the coaxial lines for the direct flow (9) and the return flow (10) of the cryogenic medium. Truncated connecting elements (30, 31) which correspond with one another are provided inside the line (10) for the return flow of the cryogenic medium (29), the line (10) being surrounded with external, vacuum and thermally isolating cases (32, 33), and truncated connecting elements (34, 35) which also correspond with one another are provided within line (9) for the direct flow of the cryogenic medium (29), and an electric line (36) is provided for electrical connection or interruption between the two lines (9, 10).

The truncated connecting elements (30, 31) are rigidly connected to the external vacuum and thermally isolating cases (32, 33) inside the line (10) for the return flow of the cryogenic medium (29) and the truncated connecting element (34) is immovable and the truncated connecting element (35) is rigidly connected to a wall (37) of the line (9) but movable in axial direction against the force of a spring (38), preferably up to 1.5 mm.

With a closed electrical connection, the truncated connecting elements (30, 31) of the line (10) are permanently compressed by means of a bayonet coupling consisting of a vacuum space (39), a tongue (40) with a joint (41) and a locking screw (42), a spring (44) being located between the movable tongue (40) and a stationary support (43).

The truncated connecting elements (30, 31, 34, 35) are formed at an acute angle of preferably 12° to 6°.

To connect the electric line (36), two cylindrical hollow elements (45, 46) are pushed into one another between the two coaxial lines (9, 10), the external cylindrical element (45) being preferably provided with stop faces.

The external cylindrical element (45) is structured for accurate clamping onto the internal cylindrical element (46), preferably with 4 furrows having a length amounting to $\frac{2}{3}$ of the overall length of the element (45).

For secure clamping, the outer diameter of the internal cylindrical element (46) is smaller by 0.3 mm than the inner diameter of the external cylindrical element (45).

What is claimed is:

1. A cryogenic assembly for use in medical treatments, said cryogenic assembly including a cryoapplicator for application of a cryogenic medium to a surface, a cryostat for supply of cryogenic medium, an elongated cryotube for conveying cryogenic medium from said cryostat to said cryoapplicator, and a connecting device connecting said cryotube with said cryoapplicator, said elongated cryotube comprising a supply conduit for conveying cryogenic medium from said cryostat to said cryoapplicator; a discharge conduit for conveying cryogenic medium away from said cryoapplicator; a first electromagnetic valve for controlling flow of cryogenic medium through said supply conduit, said first electromagnetic valve being located in said cryotube a distance from said cryoapplicator less than $\frac{1}{12}$ a length of said cryotube; and a first heating device between the first electromagnetic valve and said connecting device for heating cryogenic medium in said supply line, and said cryostat comprising a second electromagnetic valve for supply of liquid cryogenic medium, a third electromagnetic valve for controlling supply of gaseous cryogenic medium, a fourth electromagnetic valve for regulating excess pressure of cryogenic medium, a second heating device for heating cryogenic medium, a level sensor for detecting a level of cryogenic medium, and a pressure sensor for detecting a pressure of cryogenic medium in said cryostat.

2. A cryogenic assembly according to claim 1, including a regulating device connected to said first, second, third and fourth electromagnetic valves, said pressure sensor and said first heating device for regulating excess pressure of cryogenic medium in said cryostat to an accuracy of $\pm 0.1 \times 10^5$ Pa.

3. A cryogenic assembly according to claim 1, including a first temperature sensor in said cryoapplicator for enabling the regulating device to control a temperature on a working surface of the cryoapplicator to an accuracy of ±1° C. by operation of said first electromagnetic valve.

4. A cryogenic assembly according to claim 1, wherein said first electromagnetic valve is located in said cryotube a distance from said connecting element less than 1/14 the length of said cryotube.

5. A cryogenic assembly according to claim 1, including a third heating element for heating cryogenic medium in said discharge conduit prior to discharge to atmosphere.

6. A cryogenic assembly according to claim 1, wherein said cryostat comprises an external housing defining an opening; an inner container within the external housing that includes a side wall, an upper wall and a neck which extends to said opening, a vacuum space being defined between said inner container and said external housing; and a pump-down device connected to said external housing; said side wall being made of aluminum alloy etched on a side thereof facing the vacuum space so that residual gases are sorbed at low temperatures in the vacuum space and thus the necessary pressure of cryogenic medium in the inner container to be maintained.

7. A cryogenic assembly according to claim 6, wherein said neck of said inner container is made of stainless steel, and said upper wall is formed of a diffusion bonded bimetallic plate consisting of an upper plate of stainless steel and a lower plate of aluminum alloy.

8. A cryogenic assembly according to claim 1, wherein said supply conduit is located within said discharge conduit, wherein said discharge conduit includes a truncated connecting element at an end thereof which sealingly connects with a truncated end of an outer conduit located in said connecting device, wherein said supply conduit includes a truncated connecting element at an end thereof which sealingly connects with a truncated end of an inner conduit located in said outer conduit in said connecting device, wherein said discharge conduit and said outer conduit are respectively encased within outer cases to provide a vacuum and thermally insulating space therebetween, and including an electric line for connection or interruption between the supply conduit and the inner conduit.

9. A cryogenic assembly according to claim 8, wherein the truncated connecting elements are rigidly connected to the external vacuum and thermally isolating cases inside the discharge conduit for the return flow of cryogenic medium and the truncated connecting element is immovable and the truncated connecting element is rigidly connected to a wall of the supply conduit but movable in axial direction against the force of a spring.

10. A cryogenic assembly according to claim 8, wherein, with a closed electrical connection, the truncated connecting elements of the discharge conduit are permanently compressed by means of a bayonet coupling consisting of a vacuum space, a tongue with a joint and a locking screw, a spring being located between the movable tongue and a stationary support.

11. A cryogenic assembly according to claim 8, wherein the truncated connecting elements are formed at an acute angle of 12° to 6°.

12. A cryogenic assembly according to claim 8, wherein to connect the electric line, two cylindrical hollow elements are pushed into one another between the two coaxial lines, the external cylindrical element being provided with stop faces.

13. A cryogenic assembly according to claim 12, wherein the external cylindrical element is structured for accurate clamping onto the internal cylindrical element with four furrows having a length amounting to 2/3 of the overall length of the element.

14. A cryogenic assembly according to claim 12, for secure clamping, wherein the outer diameter of the internal cylindrical element is smaller by 0.3 mm than the inner diameter of the external cylindrical element.

* * * * *